United States Patent [19]
List et al.

[11] Patent Number: 4,801,455
[45] Date of Patent: Jan. 31, 1989

[54] PHARMACEUTICAL FORMULATION AND PROCESS FOR ITS PREPARATION

[75] Inventors: Paul H. List; Peter C. Schmidt; Klaus-Jürgen Steffens, all of Marburg; Harald Perschbacher, Bad Homburg; Hans P. Kraemer, Marburg; Hans H. Sedlacek, Marburg, all of Fed. Rep. of Germany

[73] Assignee: Behringwerke Aktiengesellschaft, Marburg, Fed. Rep. of Germany

[21] Appl. No.: 71,382

[22] Filed: Jul. 9, 1987

[30] Foreign Application Priority Data

Jul. 11, 1986 [DE] Fed. Rep. of Germany ....... 3623376

[51] Int. Cl.[4] .......................... A61K 9/10; A61K 9/14; A61K 47/00
[52] U.S. Cl. .................................... 424/400; 514/937; 514/939; 514/943
[58] Field of Search ....................... 514/937, 939, 943; 424/400

[56] References Cited

U.S. PATENT DOCUMENTS 4,563,354  1/1986  Chang et al. ................... 514/938

FOREIGN PATENT DOCUMENTS 0212875  3/1987  European Pat. Off. .
1155036  6/1969  United Kingdom .

OTHER PUBLICATIONS

Vigne et al CA.106:201766k (1987) of PCT. WO870/035, Feb. 26, 1987.
Rabiner et al CA.106:72843g (1987) of Tenside, Surfactants, Deterg. (1986) 23(6): 342-5.
Mizushima et al CA.102:137811j (1985) of EPO 129435. Dec. 27, 1984.
Hansrani et al., Journal of Parenteral Science and Technology, vol. 37 No. 4, 1988, pp. 145–150.
Yalkowsky, Techniques of Solubilization of Drugs, Marcel Dekker, Inc., New York, 1981.
Olesen et al., British Journal of Anaesth., vol. 52, 1980, pp. 609–611.
Repta, Topics in Pharmaceutical Sciences, 1981, pp. 131–151.
Black et al., Drug Intelligence and Clinical Pharmacy, vol. 15, 1981, pp. 185–193.
Milner et al., Science, vol. 3, 1950, pp. 633–635.

Primary Examiner—Shep K. Rose
Attorney, Agent, or Firm—Finnegan, Henderson, Farabow, Garrett, & Dunner

[57] ABSTRACT

A pharmaceutical formulation for the parenteral, in particular intravenous, administration of sparingly soluble substances is obtained when the very finely ground substance, with a maximum particle diameter of 3 μm, is dispersed in an oil phase which contains emulsifier, and this mixture is emulsified with water for injection, is rendered isotonic and is homogenized using a high-pressure homogenizer, so that the resultant product is a solid/liquid/liquid disperse system.

5 Claims, No Drawings

PHARMACEUTICAL FORMULATION AND PROCESS FOR ITS PREPARATION

The invention relates to a pharmaceutical formulation for the parenteral administration of substances which are very sparingly soluble in physiologically tolerated hydrophilic and lipophilic media, which formulation is prepared by dispersing the substance, which has been very finely ground, in the oil phase, followed by emulsification and homogenization.

The preparation of emulsions which can be administered parenterally is described by, for example, Hansrani (P. K. Hansrani, S. S. Davis, M. J. Groves, J. Parenter, Sci. Technol., 37, 145 (1983)). This entails a vegetable oil being emulsified in water, using an emulsifier, usually lecithin, and high-pressure homogenization being used to obtain a particle size of less than one micrometer. The final product in this process is in the form of a liquid/liquid system.

Numerous formulations for the intravenous administration of sparingly soluble substances have been described. For example, it is possible for these substances to be induced to dissolve using cosolvents or to be solubilized in micelles (Techniques of Solubilizing Drugs, S. H. Yalkowski ed., 1981, Marcel Dekker, New York, pages 15–134). These two possibilities have, in respect of tolerability, distinct disadvantages compared with the emulsion formulations which contain the active compound, for example diazepam (commercial product Diazemuls®, Kabivitrum, FRG marketed since Jan. 1, 1983) dissolved in the oil phase (A. S. Olesen, M. S. Hüttel, Br. J. Anaesth. 52, 609, 1980)).

Other processes make use of parenteral nutrient emulsions as vehicles and add the substance dissolved in a cosolvent, which may give rise to complications on intravenous administration (A. J. Repta, Topics in Pharmaceutical Sciences, D. D. Breimer and P. Speiser ed., 1981, page 131, Elsevier/North-Holland Biomedical Acss.).

The methods to date for the intravenous administration of particles using colloidal pharmaceutical vehicles, such as Liposomes or nanocapsules, have the disadvantage that they allow the administration of only small amounts of substance, and some of them are composed of materials which can be only slowly biotransformed, such as cyanoacrylates.

The invention has the object of developing, for substances which are very sparingly soluble in physiologically tolerated hydrophilic and lipophilic media, a formulation which is well tolerated, allows intravenous administration of high doses, can be employed for as many substances as possible, and is stable, at least in the short term.

The object is achieved according to the invention by a pharmaceutical formulation which is composed of a solid/liquid/liquid disperse system with a maximum particle size of 5 $\mu$m and which is obtained by dispersing up to 1.5% by weight of very finely ground (for example by wet grinding in a stirred ball mill) substance with a particle size not exceeding 3 $\mu$m in 8–30% by weight of oil phase which contains 1.0–4.5% by weight of emulsifier, based on the total mixture, and emulsifying this mixture with 64–90% by weight of water for injection, rendering isotonic, and homogenizing using a high-pressure homogenizer.

Suitable for the processing according to the invention are substances which are poorly soluble in oily and aqueous media, such as, for example, certain cytostatics, antibiotics and spironolactone. The amounts which are to be used depend on a variety of factors, including the efficacy of the substance and range of indications. Thus, it is difficult to make a general statement of them.

However, in most cases it will be preferred to use more than 0.03% by weight and not more than 1.5% by weight of substance.

It is possible to use as oil phase all lipophilic media which can be used pharmaceutically for injection products, such as, for example, cottonseed oil, arachis oil, ethyl oleate, isopropyl myristate, corn oil, medium chain-length triglycerides, olive oil, castor oil, soybean oil and hydrogenated liquid vegetable oils. Miglyol® 812 (saturated triglycerides with $C_8$–$C_{12}$ fatty acids) is preferably used in amounts of, preferably, 9 to 20% by weight of the total formulation.

It is possible to use as emulsifier, or component of an emulsifier mixture, emulsifiers which are tolerated on parenteral administration, such as egg lecithins, soybean lecithins, hydrogenated egg lecithins, hydrogenated soybean lecithins, cholesterol, acetylated monoglycerides and polyethylene glycol/polypropylene glycol block polymers. Soybean lecithins are preferably used in amounts of, preferably, 1.3 to 3.0% by weight of the total formulation.

For rendering isotonic, use is made of not only preferably monovalent electrolytes, for example NaCl, but also non-ionic additives such as, for example, glycerol, mannitol, sorbitol and xylitol. NaCl is preferably used, and the amount which is preferably used is between 0.5 and 0.81% by weight of the total formulation.

In principle, all processes with which a particle fineness of less than 5 $\mu$m can be achieved without the solid particles leaving the oil phase are suitable for the homogenization. Since, on the industrial scale, parenteral emulsions are brought to the necessary particle fineness by high-pressure homogenization, and there is a risk of decomposition of the active compounds or auxiliaries on exposure to ultrasound, use is preferably made of high-pressure homogenization.

It has been shown that the combination of the additive for rendering isotonic and the emulsifier has an effect on whether the active compound particles remain in the oil phase. Thus, it has emerged that on use of, preferably, monovalent electrolytes, for example NaCl, as additive for rendering isotonic, and of lecithin or lecithin and cholesterol as emulsifier, the solid particles do not leave the oil phase, and the particles are, despite the addition of electrolyte, in the size range of smaller than 5 $\mu$m which is required for emulsions for intravenous administration, although—as is known from the literature—emulsions stabilized with lecithin may be destabilized by electrolytes (C. D. Black, N. G. Popovich, Drug Intell. Clin. Pharm., 15, 185 (1981)). On the other hand, where hydrogenated lecithin, preferably Epikuron® 200H, was used, the addition of a non-ionic agent for rendering isotonic was more favorable. Hence, the emulsifier and the substance for rendering isotonic are preferably used in the formulation according to the invention in such a way that electrolytes are combined with lecithin or lecithin and cholesterol, and non-ionic agents for rendering isotonic are combined with hydrogenated lecithin.

The particular advantages of the formulation according to the invention are that it is well tolerated owing to the exclusive use of substances which are well tolerated physiologically, that there is no exposure of the substances to heat during the preparation, and there is prevention of decomposition reactions in the aqueous phase (A. J. Repta, Topics in Pharmaceutical Sciences, D. D. Breimer and P. Speiser ed. 1981, page 131, Elsevier/North-Holland Biomedical Press).

The general basic formulation which can be used is:

Active compound: up to 1.5% by weight, preferably up to 0.5% by weight

Oil phase: 8-30% by weight, preferably 9-20% by weight

Emulsifier: 1-4.5% by weight, preferably 1.3-3% by weight

Aqueous phase: 64-90% by weight, preferably 76.5-89.7% by weight.

It is possible for the preparation according to the invention to process both lecithins with a high proportion of unsaturated fatty acids, preferably Epikuron® 170 (a specially purified soybean lecithin), but in this case preferably with addition of electrolyte, as well as those with a proportion of only 10-30% of unsaturated fatty acids. The former have the advantage that emulsification and homogenization are less problematical.

Active compounds which are incorporated in the formulation according to the invention show a clearly measurable effect after one parenteral administration. The extent of release depends on the composition of the emulsifier. Intravenous administration of the particles is well tolerated, and thus the formulation is also suitable for parenteral administration for screening purposes in animal experiments.

The preparation of the formulation according to the invention is illustrated in detail in the examples which follow:

EXAMPLE 1

|  | Batch size (g) |
| --- | --- |
| Dihydroxyanthraquinone | 0.200 |
| Miglyol ® 812 | 3.800 |
| Epikuron ® 170 | 0.480 |
| Cholesterol | 0.048 |
| 0.9% NaCl | 35.472 |
|  | 40.000 |

A 10% strength suspension of dihydroxyanthraquinone in Miglyol ® 812 was ground to a particle size of less than 3 μm in a Dyno-Mill type KDL (continuous operation, circumferential speed 10 m/s, time 60 min, 0.3 mm glass beads). An amount of the suspension containing the necessary amount of dihydroxyanthraquinone was mixed with Miglyol ® 812 in an Erlenmeyer flask to produce one half of the total oil phase, and the mixture was made up with a 24% strength solution of the lecithin in Miglyol ® 812. Thereafter, first cholesterol and then water for injection was added, stirring continuously, and when emulsification was complete the sodium chloride was added. The high-pressure homogenization was carried out in a French pressure cell (Millner, Lawrence, French, Science, 3, 633, 1950) which was additionally equipped with a fine control valve.

The homogenization was carried out under a pressure of 550 bar and with a slit width of 35 μm.

EXAMPLE 2

|  | Batch size (g) |
| --- | --- |
| S830544 | 0.0124 |
| Miglyol ® 812 | 3.9876 |
| Epikuron ® 170 | 0.48 |
| Cholesterol | 0.048 |
| NaCl (0.9%) | 35.472 |
|  | 40.000 |

The chemical name of S830544 is 1,4-bis(dl-2,3-oxidopropoxy)anthraquinone. Preparation as for Example 1. Homogenization with 320 bar, 150 μm slit and 3 passages.

An animal test was carried out to investigate the cytostatic action of the substance. Test groups each comprising 6 BDF1 mice (18-20 g) were formed, and the mice received $10^6$ L1210 Leukemia cells by i.p. administration one day before the start of the test. Each group received i.p. administration of a particular dose once a day during the 5-day test.

The median survival time (MST) in the individual test groups was evaluated. The percentage prolongation of life was obtained by dividing by the median survival time in the control group without administration of substance, multiplied by 100. Figures above 125% indicated a cytostatic action. The occurrence or absence of ascites was used to assess the cause of death. The occurrence of ascites was caused by the L1210 leukemia cells, and thus it was possible to differentiate between the toxicity of the test substance and that of the tumor.

| Dosage | MST/contr. % | Ascites |
| --- | --- | --- |
| 7.75 mg/kg body weight | 114 | 4 of 6 |
| 4.65 mg/kg body weight | 143 | 5 of 6 |
| 1.55 mg/kg body weight | 129 | 6 of 6 |

The results show that the formulation according to the invention makes it possible straightforwardly and without difficulty to administer therapeutically relevant amounts of substance, and that the incorporated substance is released in therapeutically relevant concentrations from the formulation according to the invention. The prolongation of life found with the middle dosage clearly exceeded the criterion of efficacy. As the dose increases the significance of the toxicity of the substance increases in comparison with that of the tumor.

Comparison of the results obtained with those of earlier tests reveals that the onset of action takes place at much lower doses with the formulation according to the invention.

| Dosage | MST/contr. % | Ascites |
| --- | --- | --- |
| 1 × 1000 mg/kg body weight | 81 | 1 of 6 |
| 1 × 800 mg/kg body weight | 81 | 3 of 6 |
| 1 × 600 mg/kg body weight | 95 | 6 of 6 |
| 1 × 400 mg/kg body weight | 95 | 6 of 6 |
| 1 × 200 mg/kg body weight | 100 | 6 of 6 |

To carry out these tests, before the i.p. administration of the substance it was dispersed in a surfactant-containing medium and homogenized with ultrasound.

EXAMPLE 3

|  | Batch size (g) |
| --- | --- |
| S827942 | 0.128 |
| Miglyol ® 812 | 3.872 |
| Epikuron ® 170 | 0.48 |
| Cholesterol | 0.048 |
| NaCl 0.9% | 35.472 |
|  | 40.000 |

The chemical name of S827942 is 3-methyl-9-((2-methoxy-4-methylsulfonylamino)anilino)thieno[3,2-b]quinoline lactate. Preparation, homogenization conditions and substance testing in analogy to Example 2.

| Dosage | MST/contr. % | Ascites |
| --- | --- | --- |
| 80 mg/kg body weight | 157 | 0 of 6 |
| 48 mg/kg body weight | 157 | 0 of 6 |
| 16 mg/kg body weight | 157 | 6 of 6 |
| 8 mg/kg body weight | 129 | 6 of 6 |
| 1.6 mg/kg body weight | 129 | 6 of 6 |

Example 3 likewise demonstrates that the incorporated substance is released in effective concentrations. Comparison of these results with those of earlier tests shows that the cytostatic action on preparation according to the invention is detectable at far lower doses.

| Dosage | MST/contr. % | Ascites |
| --- | --- | --- |
| 1 × 800 mg/kg body weight | 138 | 4 of 10 |
| 1 × 700 mg/kg body weight | 149 | 7 of 10 |
| 1 × 600 mg/kg body weight | 154 | 9 of 10 |
| 1 × 500 mg/kg body weight | 147 | 10 of 10 |
| 1 × 400 mg/kg body weight | 147 | 10 of 10 |
| 1 × 300 mg/kg body weight | 151 | 10 of 10 |

The preparation was prepared in analogy to Example 2 by dispersion of the substance in a surfactant-containing medium, followed by homogenization with ultrasound.

EXAMPLE 4

|  | Batch size (g) |
| --- | --- |
| Spironolactone | 0.288 |
| Miglyol ® 812 | 7.712 |
| Epikuron ® 170 | 1.2 |
| Cholesterol | 0.12 |
| 0.9% NaCl | 30.68 |
|  | 40.000 |

The preparation was carried out in analogy to Example 1. Homogenization with 660 bar, 150 μm slit and 3 passages.

An animal test was carried out to investigate the diuretic action of the preparation. Test groups each comprising 3 Lewis rats (160–180 g) were formed and accommodated in metabolism cages. During the 4-day test, the animals received food and water as required, and the amount of urine excreted was measured every 24 hours. Various control groups were formed to improve the assessment of the results:
 without administration
 blank formulation i.p.
 blank formulation i.v.

| Preparation | Dosage mg/kg body weight | Urine excretion ml/rat/h 0-24 | 24-48 | 48-72 | 72-96 | Cumulative urine excretion per rat after 96 h (ml) |
| --- | --- | --- | --- | --- | --- | --- |
| Spironolactone | 25 i.p. | 0.42 | 0.44 | 0.28 | 0.3 | 34.56 |
| Spironolactone | 50 i.p. | 0.8 | 0.58 | 0.55 | 0.56 | 60.48 |
| Blank formulation | 1 ml i.p. | 0.16 | 0.2 | 0.25 | 0.28 | 21.12 |
| Spironolactone | 50 i.v. | 0.6 | 0.55 | 0.39 | 0.3 | 44.16 |
| Blank formulation | 1 ml i.v. | 0.47 | 0.36 | 0.38 | 0.33 | 35.1 (90 h) |
| Without administration |  | 0.33 | 0.25 | 0.16 | 0.25 | 24 |

Spironolactone is released in therapeutically relevant concentrations from the formulation according to the invention. The results data demonstrate that the diuretic action found after i.p. administration is more pronounced and long-lasting than after i.v. administration. The amount of urine excreted is about 25% higher than in the group with i.v. administration of the blank formulation whereas an increase of about 185% is detectable on i.p. administration.

EXAMPLE 5

|  | Batch size (g) |
| --- | --- |
| Spironolactone | 0.288 |
| Miglyol ® 812 | 7.712 |
| Epikuron ® 200H | 0.96 |
| Epikuron ® 170 | 0.24 |
| 2.5% glycerol | 30.8 |
|  | 40.000 |

The preparation was carried out in analogy to Example 1. Homogenization with 300 bar, 100 μm slit width and 3 passages.

The animal test was carried out under the same conditions as for Example 4.

| Preparation | Dosage (mg/kg body weight) | Urine excretion ml/rat/h 0-24 | 24-48 | 48-72 | 72-90 | Cumulative urine excretion per rat after 90 h (ml) |
| --- | --- | --- | --- | --- | --- | --- |
| Spironolactone | 50 i.p. | 0.5 | 0.42 | 0.36 | 0.33 | 36 |
| Blank formulation | 1 ml i.p. | 0.28 | 0.31 | 0.32 | 0.3 | 27 |
| Spironolactone | 50 i.v. | 0.44 | 0.42 | 0.48 | 0.63 | 44.1 |
| Blank formulation i.v. | 1 ml i.v. | 0.47 | 0.36 | 0.36 | 0.36 | 35.1 |
| Without administration |  | See Example 4 |  |  |  | See Example 4 |

An increase in diuresis compared with the control groups is also detectable in Example 5. However, it is noticeable that the increase in diuresis on i.p. administration is distinctly lower than in Example 4, and that there is a delay in the occurrence of the maximum effect after i.v. administration. These effects are attributable to the variation in the lecithin component. Apparently release takes place more rapidly and completely the higher the content of unsaturated fatty acids in the lecithin component.

We claim:

1. An isotonic pharmaceutical formulation for the parenteral administration of a sparingly soluble pharmaceutically active substance, composed of a solid/liquid/liquid disperse system with a maximum particle size of 5 μm, said disperse system being a dispersion of an amount sufficient for efficacy up to 1.5% by weight of the sparingly soluble active substance having a particle size not exceeding 3 μm in 8–30% by weight of oil phase which contains 1.0–4.5% by weight of emulsifier, based on the total mixture, said mixture being an emulsion with 64–90% by weight of water.

2. An isotonic pharmaceutical formulation as claimed in claim 1, in which the formulation is rendered isotonic by a monovalent electrolyte, and the emulsifier is lecithin or lecithin and cholesterol.

3. A pharmaceutical formulation as claimed in claim 1, in which the formulation is rendered isotonic by a non-ionic substance, and the emulsifier is hydrogenated lecithin.

4. A process for the preparation of a pharmaceutical formulation for the parenteral administration of a sparingly soluble active substance, which comprises dispersing an amount sufficient for efficacy up to 1.5% by weight of the sparingly soluble active substance having a particle diameter not exceeding 3 μm in 8–30% by weight of oil phase which contains 1.0–4.5% by weight of emulsifier, based on the total mixture, and emulsifying this mixture with 64–90% by weight of water for injection, rendering the resultant emulsion isotonic, and homogenizing the emulsion whereby the resultant product is a solid/liquid/liquid disperse system having a maximum particle diameter of 5 μm.

5. A pharmaceutical formulation as claimed in claim 1, in which the formulation is in an homogenized state.

* * * * *